United States Patent [19]

Kerr

[11] 4,202,826

[45] * May 13, 1980

[54] PROCESS FOR PREPARING ANHYDRIDE FROM ALKANES

[75] Inventor: Ralph O. Kerr, Houston, Tex.

[73] Assignee: Denka Chemical Corporation, Houston, Tex.

[*] Notice: The portion of the term of this patent subsequent to Nov. 1, 1994, has been disclaimed.

[21] Appl. No.: 898,663

[22] Filed: Apr. 21, 1978

Related U.S. Application Data

[62] Division of Ser. No. 767,499, Feb. 10, 1977, Pat. No. 4,105,586.

[51] Int. Cl.$^2$ .............................................. C07D 307/60
[52] U.S. Cl. ............................... 260/346.75; 260/333; 260/345.9 R
[58] Field of Search ..................................... 260/346.75

[56] References Cited

U.S. PATENT DOCUMENTS

| | | | |
|---|---|---|---|
| 3,156,705 | 11/1964 | Kerr | 260/346.45 |
| 3,297,587 | 1/1967 | Scherhag et al. | 252/432 |
| 3,875,220 | 4/1975 | White et al. | 260/530 N |
| 3,956,181 | 5/1976 | Grasselli et al. | 252/432 |
| 3,980,585 | 9/1976 | Kerr et al. | 252/437 |
| 4,056,487 | 11/1977 | Kerr | 252/435 |

*Primary Examiner*—Alan L. Rotman
*Assistant Examiner*—Bernard Dentz
*Attorney, Agent, or Firm*—Kenneth H. Johnson

[57] ABSTRACT

A catalyst complex useful for the partial oxidation of alkanes to the corresponding anhydrides, e.g., converting normal $C_4$ hydrocarbons to maleic anhydrides, e.g., converting normal $C_4$ hydrocarbons to maleic anhydride in vapor phase, comprising as components vanadium, phosphorus, oxygen, Nb. Cu, Mo, Ni, Co and Cr. Preferred are those compositions containing in addition one or more of Ce, Nd, Ba, Hf, U, Ru, Re, Li or Mg.

10 Claims, No Drawings

PROCESS FOR PREPARING ANHYDRIDE FROM ALKANES

This is a division, of application Ser. No. 767,499 filed Feb. 10, 1977 now U.S. Pat. No. 1,105,586.

BACKGROUND OF THE INVENTION

The present invention relates to an improved process for the preparation of dicarboxylic anhydride from $C_4$-$C_{10}$ hydrocarbons preferably using a feed containing major amounts of alkanes, by the reaction of oxygen with the hydrocarbon in vapor phase over a particular novel catalyst, such as the preparation of maleic anhydride from butane.

The production of dicarboxylic acid anhydride by catalytic oxidation of hydrocarbons is well known. The current principal route for the production of maleic anhydride from $C_4$ hydrocarbons has been desirable in the past, but is now even more desirable in view of the particular world shortage of benzene. It can be readily appreciated that direct oxidation of $C_4$ hydrocarbons would be a hydrocarbon conservation, since for each mol of maleic anhydride prepared from benzene, one mol of benzene, molecular weight 78 is consumed, whereas for each mol of the $C_4$, only 54 to 58 mol weight of hydrocarbon is consumed. The benzene process has consistently produced high conversions and selectivities. Although processes for the oxidation of aliphatic hydrocarbons are reported in the literature, there are certain defects and inadequacies in these processes, such as short catalyst life and low yields of product. Furthermore, although many of the prior art methods are generically directed to "aliphatic" hydrocarbons, they are in all practical aspects directed to unsaturated aliphatic hydrocarbons.

A more desirable process for producing maleic anhydride would be a direct oxidation of n-butane. There are several advantages. Principal among these is the greater availability of n-butane as compared to n-butenes or butadiene. Also, n-butenes may have higher economic petrochemical utilization than the n-butanes, which are now, often wastefully burned as cheap fuel.

In an early series of patents, the present inventor developed a unique group of vanadium-phosphorus, oxidation catalysts, i.e., U.S. Pat. Nos. 3,156,705; 3,156,706; 3,255,211; 3,255,212; 3,255,213; 3,288,721; 3,351,565; 3,366,648; 3,385,796 and 3,484,384. These processes and catalysts proved highly efficient in the oxidation of n-butenes to maleic anhydride. Since the issuance of these pioneer patents, numerous patents have issued with various modification and improvements over the basic discoveries set forth there, e.g., U.S. Pat. Nos. 3,856,824; 3,862,146; 3,864,280; 3,867,411 and 3,888,886.

Most recently, the present inventor discovered that vanadiumphosphorus-oxygen complex type catalyst modified with a particular group of components is an excellent oxidation catalyst for the conversion of $C_4$ to $C_{10}$ hydrocarbons to the corresponding anhydrides, particularly, n-$C_4$ hydrocarbons to maleic anhydride, which is disclosed and claimed in U.S. Pat. No. 4,056,487 issued Nov. 1, 1977. In addition to n-butane, n-butene and butadiene may also be used as feeds. The catalyst contains only a minor amount of the modifying component. The essential elements of the modifying component are Nb, Cu, Mo, Ni, Co and Cr. In addition to the essential elements, the modifying component may contain one or more elements from the group of Ce, Nd, Ba, Hf, U, Ru, Re, Li or Mg. The elements comprising the modifying components are metal or metalloid in characterization.

SUMMARY OF THE INVENTION

Very briefly, what the present inventor has discovered is an additional group of modifying elements selected from the group consisting of Y, Sm, Tb and Eu. That is, the present invention is a vanadiumphosphorus-oxygen complex type catalyst for the conversion of $C_4$ to $C_{10}$ hydrocarbons to the corresponding anhydrides in which the catalyst contains the essential modifying elements of Nb, Cu, Mo, Ni, Co and Cr, and one or more of the elements selected from the group consisting of Y, Sm, Tb and Eu. In addition to these newly discovered modifiers, the catalyst may also contain one or more of the elements from the group consisting of Ce, Nd, Ba, Hf, U, Ru, Re, Li or Mg. The preferable components from my prior compositions, which are additionally present, are one or more of the elements selected from the group consisting of Ce, Nd and B. The improved catalyst containing these modifiers include those that have demonstrated superior performance.

One type of preferred catalyst contains in the modifier, Y and Sm, preferably with the addition of Nd, Ce and Ba.

The precise structure of the present complex catalyst has not been determined; however, the complex may be represented by formula

$$VP_aMe_bO_x$$

wherein Me is the modifying component described above, a is 0.90 to 1.3, b is 0.005 to 0.4. This representation is not an empirical formula and has no significance other than representing the atom ratio of the active metal components of the catalyst. The x, in fact, has no determinate value and can vary widely, depending on the combinations within the complex. That there is oxygen present is known and the $O_x$ is representative of this.

The following listing shows the ranges of each member of the complex, including the modifying component. The relative proportions are shown in atomic ratio relative to vanadium which is designated as 1.

The amounts of components are selected within these ranges so that the total atoms of modifying component stays within the range given above, i.e., 0.005 to 0.4 atom per atoms of vanadium.

| Catalyst Component | Atomic Ratio |
|---|---|
| V | 1 |
| P | 0.90 - 1.3 |
| Nb | 0.001 - 0.125 |
| Cu | 0.022 - 0.201 |
| Mo | 0.0025 - 0.040 |
| Ni | 0.0022 - 0.045 |
| Co | 0.0040 - 0.066 |
| Ce | 0.0054 - 0.20 |
| Nd | 0.0022 - 0.20 |
| Cr | 0.0003 - 0.003 |
| Ba | 0.0023 - 0.0585 |
| Hf | 0.0023 - 0.0409 |
| U | 0.0033 - 0.0993 |
| Ru | 0.0002 - 0.02015 |
| Re | 0.0002 - 0.0074 |
| Li | 0.0072 - 0.179 |
| Mg | 0.0088 - 0.222 |

-continued

| Catalyst Component | Atomic Ratio |
|---|---|
| Y | 0.0001 - 0.02 |
| Sm | 0.0001 - 0.02 |
| Tb | 0.0001 - 0.02 |
| Eu | 0.0001 - 0.02 |

The relative amounts of the elements in the modifier as embraced by this species are set forth above and when combined with the essential components give a total of 0.005 to 0.4 atom of modifier per atom of vanadium, preferably, at least 0.033 of modifier per atom of vanadium.

The oxygen atomic ratio may vary widely, generally in the range of 5 to 8, for the catalyst compositions of the present invention.

DETAILED DESCRIPTION OF THE INVENTION

The catalyst may be prepared in a number of ways. The catalyst may be prepared by dissolving compounds of vanadium, phosphorus, and other compound components, i.e., Nb, Cu, Mo, Ni, Co, Ce, Nd, Cr, Ba, Hf, U, Ru, Re, Y, Sm, Tb, Eu, Li or Mg in a common solvent, such as hot hydrochloric acid and thereafter depositing the solution onto a carrier. The catalyst may also be prepared by precipitating the various compounds, either with or without a carrier from a colloidal dispersion of the ingredients in an inert liquid. In some instances, the catalyst may be deposited as molten various compounds onto a carrier; however, care must be taken not to vaporize off any of the ingredients such as phosphorus. The catalyst may also be prepared by heating and mixing anhydrous forms of phosphorus acids with vanadium compounds and compounds of the other components. The catalyst may be used as either fluid bed or fixed bed catalysts. In any of the methods of preparation, heat may be applied to accelerate the formation of the complex.

One method to obtain catalyst comprises forming the catalyst complex in solution and deposited as a solution onto niobium oxide ($Nb_2O_5$). According to one solution method, the vanadium is present in solution with an average valence of less than plus 5 in the finally formed complex in solution. Preferably, the vanadium has an average valency of less than plus 5 at the time the solution of catalyst complex is deposited onto the carrier, if a carrier is used. The reduced vanadium with a valence of less than 5 may be obtained either by initially using a vanadium compound wherein the vanadium has a valence of less than 5, such as vanadyl chloride, or by initially using a vanadium compound with a valence of plus 5, such as $V_2O_5$, and thereafter reducing to the lower valence with, for example, hydrochloric acid during the catalyst preparation to form the vanadium oxysalt, vanadyl chloride, in situ. The vanadium compound may be dissolved in a reducing solvent, such as hydrochloric acid, which solvent functions not only to form a solvent for the reaction, but also to reduce the valence of the vanadium compound to a valence of less than 5. Preferably, the vanadium compound is first dissolved in the solvent and thereafter the phosphorus and other metal (metalloid) compounds are added. The reaction to form the complex may be accelerated by the application of heat. The deep blue color of the solution shows the vanadium has an average valence of less than 5. The complex formed is then, without a precipitation step, deposited as a solution onto the $Nb_2O_5$ and dried. In this procedure, the vanadium has an average valence of less than plus 5, such as about plus 4, at the time it is deposited onto the $Nb_2O_5$. Generally, the average valence of the vanadium will be between about plus 2.5 and 4.6 at the time of deposition onto the carrier.

When the above described solution method is employed, reducing agents for the vanadium may be either organic or inorganic. Acids such as hydrochloric, hydroiodic, hydrobromic, acetic, oxalic, malic, citric, formic and mixtures thereof, such as a mixture of hydrochloric and oxalic may be used. Sulfur dioxide may be used. Less desirably, sulfuric and hydrofluoric acids may be employed. Other reducing agents which may be employed, but which have not been given as desirable catalysts are organic aldehydes such as formaldehyde and acetaldehyde; alcohols such as pentaerythritol, diacetone alcohol and diethanol amine. Additional reducing agents are such as hydroxyl amines, hydrazine and nitric oxide. Nitric acid and similar oxidizing acids which would oxidize the vanadium from a valence of 4 to 5 during the preparation of the catalyst should be avoided. Generally, the reducing agents form oxysalts of vanadium. For example, if $V_2O_5$ is dissolved in hydrochloric or oxalic acid, the corresponding vanadium oxysalts are produced. These vanadium oxysalts should have as the salt forming anion, an anion which is more volatile than the phosphate anion.

Any vanadium, phosphorus and metal and metallid compounds may be used as starting materials which, when the compounds are combined and heated to dryness in air at a temperature of, for example, 300°-350° C. will leave as a deposit a catalyst complex having relative proportions within the described ranges. In the solution methods, preferred are vanadium, phosphorus and metal and metalloid (except Nb) compounds, which are essentially completely soluble in boiling aqueous hydrochloric acid at 760 mm. of mercury, containing 37 percent by weight hydrochloric acid. Generally, phosphorus compounds are used which have as the cation an ion which is more volatile than the phosphate anion, for example, $H_3PO_4$. Also, generally any vanadium or Me compound which has as an anion, an anion which is either the phosphate ion or an ion which is more volatile than the phosphate anion, for example, vanadyl chloride or copper chloride, nickel chloride or the like may be used.

In the various methods of preparation, any vanadium, phosphorus, metal and metalloid compounds may be used as starting materials which, when the compounds are combined and heated to dryness in air at a temperature of, for example, 300°-350° C., will leave as a deposit a catalyst complex having relative proportions within the above described ranges.

In another method, a solution of the vanadium component is prepared by adding a portion of a reducing agent, such as oxalic acid and isopropanol solution to a solution of water and phosphoric acid, and heating this mixture to a temperature generally of around 50°-80° C. A vanadium compound such as $V_2O_5$ is added incrementally to this heated mixture with stirring. The blue solution which indicates vanadium of average valency less than 5, is maintained by adding increments of the remaining oxalic acid-isopropanol solution. After concentration of this solution, solutions of other components are added to vanadium solution and this resultant solution concentrated to a paste-like consistency, and intimately mixed with $Nb_2O_5$, heated at moderate temperature, i.e., 200°–400° C. for a few minutes to several hours and prepared in pellets or chips.

As the source of phosphorus, various phosphorus compounds may be used, such as metaphosphoric acid, triphosphoric acid, pyrophosphoric acid, ortho-phosphoric acid, phosphorus pentoxide, phosphorus oxyiodide, ethyl phosphate, methyl phosphate, amine phosphate, phosphorus pentachloride, phosphorus trichloride, phosphorus oxybromide and the like.

Suitable vanadium compounds useful as starting materials are compounds such as vanadium pentoxide, ammonium metavanadate, vanadium trioxide, vanadyl chloride, vanadyl dichloride, vanadyl trichloride, vanadium sulfate, vanadium phosphate, vanadium tribromide, vanadyl formate, vanadyl oxalate, metavanadic acid, pyrovanadic acid, and the like. Mixtures of the various vanadium, phosphorus and metal and metalloid compounds may be used as starting materials to form the described catalyst complex.

The metal or metalloid component is also suitably introduced by employing the various compounds thereof such as the acetates, carbonates, chlorides, bromides, oxides, hydroxides, nitrates, chromates, chromites, tellurates, sulfides, phosphates and the like. The compounds are entirely conventional and those of ordinary skill in the art know these materials and can readily determine suitable compounds to prepare the catalyst, with little, if any, experimentation. A few illustrative compounds are nickel chloride, chromium sulfate, chromium trioxide, chromium chloride, barium chloride and similar compounds.

A catalyst support, if used, provides not only the required surface for the catalyst, but gives physical strength and stability to the catalyst material. The carrier or support normally has a low surface area, as usually measured from about 0.110 to about 5 square meters per gram. A desirable form of carrier is one which has a dense non-absorbing center and a rough enough surface to aid in retaining the catalyst adhered thereto during handling and under reaction conditions. The carrier may vary is size but generally is from about $2\frac{1}{2}$ mesh to about 10 mesh in the Tyler Standard screen size. Alundum particles as large as $\frac{1}{4}$ inch are satisfactory. Carriers much smaller than 10 to 12 mesh normally cause an undesirable pressure drop in the reactor, unless the catalysts are being used in a fluid bed apparatus. Very useful carriers are Alundum and silicon carbide or Carborundum. Any of the Alundums or other inert alumina carriers of low surface may be used. Likewise, a variety of silicon carbides may be employed. Silica gel may be used.

The amount of the catalyst complex on the carrier is usually in the range of about 15 to about 95 weight percent of the total weight of complex plus carrier and preferably in the range of 50 to 90 weight percent and more preferably at least 60 weight percent on the carrier. The amount of the catalyst complex deposited on the carrier should be enough to substantially coat the surface of the carrier and this normally is obtained with the ranges set forth above. With more absorbent carriers, larger amounts of material will be required to obtain essentially complete coverage of the carrier. In a fixed bed process, the final particle size of the catalyst particles which are coated on a carrier will also preferably be about $2\frac{1}{2}$ to about 10 mesh size. The carriers may be of a variety of shapes, the preferred shape of the carriers is in the shape of cylinder or spheres. Although more economical use of the catalyst on a carrier in fixed beds is obtained, as has been mentioned, the catalyst may be employed in fluid bed systems. Of course, the particle size of the catalyst used in fluidized beds in quite small, usually varying from about 10 to about 150 microns, and in such systems the catalyst normally will not be provided with a carrier, but will be formed into the desired particle size after drying from solution.

Inert diluents may be present in the catalyst, but the combined weight of the active ingredients, e.g., vanadium, oxygen, phosphorus, metal and metalloid should preferably consist essentially of at least about 50 weight percent of the composition which is coated on the carrier, if any, and preferably these components are at least about 75 weight percent of the composition coated on the carrier, and more preferably, at least about 95 weight percent.

The niobium component of the present composition is preferably niobium oxide, $Nb_2O_5$, which is intimately mixed with the other components of the catalysts, which are in solution.

In one procedure for preparing the present catalyst compositions, the vanadium component is prepared by adding a portion of a reducing agent, such as an oxalic acid with or without isopropanol, to a solution of water and phosphoric acid and heating this mixture to a temperature generally around 50°–60° C. A vanadium compound, such as $V_2O_5$ is slowly added while raising the temperature of the solution to 60°–90° C. A blue solution indicates vanadium of average valency of less than 5 at which time the molybdenum component as $MoO_3$ is added to the solution and dissolved therein.

The V-P-Mo mixture is added to a powdered $Nb_2O_5$ and mixed together at 75°–95° C. in a suitable mixer to obtain intimate contact. The remainder of the catalyst components are added to this mixture as solutions, preferably of the chloride salts, e.g., obtained by dissolving oxides and/or carbonates in HCl.

Thus, this method of catalyst preparation involves two particular aspects. First, the vanadium is reduced with a reducing agent in a solution containing phosphoric acid and second, a majority (over 50% by component) of the remaining catalyst components are employed as the chloride salts. In particular, Ni, Co, Cu, Cr, Nd, Ce, Ba, Hf, Y, Sm, Tb and Eu are employed as chloride salts. All of the metal and metalloid elements employed in preparing the catalyst, with the exception of vanadium, phosphorus and niobium may be used as the chloride salt.

The resulting mixture is dried at 85°–135° C. and broken into pieces of 4 to 20 mesh and dried further at 120°–130° C. then heated at 300° C. for an additional period of 0.5 to two or three hours. The catalyst may be used as such, but is preferably reduced to a powder and pelleted. As noted above, binders, such as stearic acid, carriers and inert fillers may be added before pelleting.

The oxidation of the $n-C_4$ hydrocarbon to maleic anhydride may be accomplished by contacting, e.g., n-butane, in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the oxidation reactors normally will contain air and about 0.5 to about 2.5 mol percent hydrocarbons, such as n-butane. About 1.0 to about 1.7 mol percent of the $n-C_4$ hydrocarbons are satisfactory for optimum yield of product for the process of this invention. Although higher concentrations may be employed, explosive hazards may be encountered. Lower concentrations of $C_4$, less than about one percent, of course, will reduce the total yields obtained at equivalent flow rates and thus are not normally economically employed. The flow rate of the gaseous stream through the reactor may be varied within rather wide limits, but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. An improved output of maleic anhydride can be obtained with various catalysts of the prior art and with those of the present invention if the feed consists essentially of $C_4$ normal alkane, i.e., about comprising 88 to 99 or more weight percent normal $C_4$ alkane and from about 1 to 12 weight percent n-butene, benzene, or a mixture thereof. A preferred feed for the catalyst of the present invention for conversion to maleic anhydride is a n-$C_4$ hydrocarbon comprising a predominant amount of n-butane and more preferably, at least 90 mol percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet, e.g., 12 feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrate eutectic constant temperature mixture. An additional method of temperature control in the laboratory is to use a metal block reactor whereby the metal surrounding the tube acts as a temperature regulating body. As will be recognized by the man skilled in the art, the heat exchange medium may be kept at the proer temperature by heat exchangers and the like. The reactor or reaction tubes may by iron, stainless steel, carbon steel, nickel, glass tubes, such as Vycor, and the like. Both carbon steel and nickel tubes have excellent long life under the conditions of the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally, the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the peak reaction temperature employed is no greater than about 100° C. above the salt bath temperature. The temperature in the reactor, of course, will also depend to some extent upon the size of the reactor and the $C_4$ concentration. Under usual operating conditions, in compliance with the preferred procedure of this invention, the temperature in the center of the reactor, measured by thermocouple, is about 375° C. to 550° C. The range of temperature preferably employed in the reactor, measured as above, should be from about 390° C. to about 460° C., and the best results are ordinarily obtained at temperatures from about 410° C. to about 450° C.

Described another way, in terms of salt bath reactors with carbon steel reactor tubes about 1.0 inch in diameter, the salt bath temperature will usually be controlled between about 350° C. to about 450° C. Under normal conditions, the temperature in the reactor ordinarily should not be allowed to go above about 450° C. for extended lengths of time because of decreased yields and possible deactivation of the novel catalyst of this invention.

The reaction may be conducted at atmospheric, super-atmospheric or below-atmospheric pressure. The exit pressure will be at least slightly higher than the ambient pressure to insure a positive flow from the reaction. The pressure of the inert gases may be sufficiently high to overcome the pressure drop through the reactor.

In one utilization of the present catalyst compositions, the oxidation is carried out at 15 to 100 psig, preferably about 20 to 50 psig, and more preferably about 25 to 40 psig.

Operating under pressure as described above, the temperature in the center of the reactor, measured by thermocouple is about 375° C. to about 550° C. with the preferred temperature range for operating according to the present invention being 430° C. to 480° C., and the best results are ordinarily obtained at temperatures from about 430° C. to about 455° C. Described another way, in terms of salt bath reactors with carbon steel reactor tubes about 1.0 inch in diameter, the salt bath temperature will usually be controlled between about 325° C. to about 440° C. Under these conditions, the temperature in the reactor ordinarily should not be allowed to go above about 450° C. for extended lengths of time because of decreased yields and possible deactivation of the novel catalyst of this invention.

The maleic anhydride may be recovered by a number of ways well known to those skilled in the art. For example, the recovery may be by adsorption in suitable media, with subsequent separation and purification of the maleic anhydride.

In the following examples, percents are by weight unless otherwise specified.

The reactor used to evaluate the catalyst compositions employed 300 milliliters of catalyst packed in a 3-foot carbon steel tube, ¾ inch inside diameter (or equivalent), with inert ¼ inch Alundum pellets on top of the catalyst material to a height ⅓ of the height of the catalyst.

The reactors were encased in a 7% sodium nitrate-40% sodium nitrite-53% potassium nitrate eutectic mixture constant temperature salt bath. The reactor was slowly warmed to 400° C. (250°–270° C. air passing over catalyst) while passing a gas stream containing 0.5 to 0.7 mol percent n-butane and air over the catalyst beginning at about 280° C. The reactor outlet was maintained at 1 psig. After the reactor had reached 390° C., the catalyst was aged by passing the n-butane-air mixture therethrough for 24 hours. The n-butane-air and temperature was increased to obtain a maximum throughput. The n-butane in the feed is increased to 1.0–1.5 mol percent to obtain 70–80% conversion. The salt bath is operated at a maximum of 420° C. The maximum throughput is achieved in relation to the maximum salt bath temperature and a maximum hot spot of about 450° C. The hot spot is determined by a probe through the center of the catalyst bed. The temperature of the salt bath can be adjusted to achieve the desired relationship between the conversion and flow rates of the n-$C_4$-air mixture. The flow rate is adjusted to about 75% conversion and the temperature relations given above. Generally, flow rates of about 70 to 120 grams of hydrocarbon feed per liter hour are used. The exit gases were cooled to about 55°–60° C. at about ½ psig. Under these conditions, about 30–50% of the maleic anhydride condenses out of the gas stream. A water scrubber recovery and subsequent dehydration and fractionation were used to recover and purify the remaining maleic anhydride in the gas stream after condensation. The combined maleic anhydride recovered is purified and recovered at a temperature of about 140°–165° C. overhead and 165° C. bottoms temperatures in a fractionator. The purified product had a purity of 99.9+ percent maleic anhydride.

EXAMPLES 1-5

| EXAMPLE 1 | | | EXAMPLE 2 | | |
|---|---|---|---|---|---|
| Ingredients: | | | Ingredients: | | |
| $V_2O_5$ | 263.37 | g | $V_2O_5$ | 270.531 | g |
| $MoO_3$ | 4.18 | g | $MoO_3$ | 4.268 | g |
| $CuCl_2 . 2H_2O$ | 44.386 | g | $CuCl_2 . 2H_2O$ | 45.279 | g |
| NiO | 3.304 | g | NiO | 3.373 | g |
| $CoCl_2 . 6H_2O$ | 11.992 | g | $CoCl_2 . 6H_2O$ | 15.306 | g |
| $CrO_3$ | 0.418 | g | $CrO_3$ | 0.5355 | g |
| $BaCl_2 . 2H_2O$ | 8.324 | g | $CeO_2$ | 2.6675 | g |
| $CeO_2$ | 5.5 | g | $Nd_2O_3$ | 2.6675 | g |
| $Nd_2O_3$ | 5.5 | g | $HfO_2$ | 4.268 | g |
| $HfO_2$ | 4.18 | g | $Sm_2O_3$ | 22.0 | g |
| $Y_2O_3$ | 166 | g | $Nb_2O_5$ | 16.5 | g |
| $Nb_2O_5$ | 5.5 | g | | | |
| EXAMPLE 3 | | | EXAMPLE 4 | | |
| Ingredient: | | | Ingredients: | | |
| $V_2O_5$ | 263.382 | g | $V_2O_5$ | 267.269 | g |
| $MoO_3$ | 5.335 | g | $MoO_3$ | 4.268 | g |
| $CuCl_2 . 2H_2O$ | 67.991 | g | $CuCl_2 . 2H_2O$ | 56.627 | g |
| NiO | 3.855 | g | NiO | 3.373 | g |
| $CoCl_2 . 6H_2O$ | 15.306 | g | $CoCl_2 . 6H_2O$ | 13.777 | g |
| $CrO_3$ | 0.5335 | g | $CrO_3$ | 0.5335 | g |
| $BaCl_2 . 2H_2O$ | 8.499 | g | $BaCl_2 . 2H_2O$ | 8.499 | g |
| $CeO_2$ | 5.5 | g | $CeO_2$ | 5.5 | g |
| $Nd_2O_3$ | 5.5 | g | $Nd_2O_3$ | 5.5 | g |
| $HfO_2$ | 4.268 | g | $HfO_2$ | 4.268 | g |
| $Tb_4O_7$ | 11.0 | g | $Eu_2O_3$ | 4.805 | g |
| $Nb_2O_5$ | 16.5 | g | $Nb_2O_5$ | 16.5 | g |
| EXAMPLE 5 | | | | | |
| Ingredients: | | | | | |
| $V_2O_5$ | 1222.459 | g | | | |
| $MoO_3$ | 24.25 | g | | | |
| $CuCl_2 . 2H_2O$ | 206.002 | g | | | |
| NiO | 17.524 | g | | | |
| $CoCl_2 . 6H_2O$ | 71.726 | g | | | |
| $CrO_3$ | 2.425 | g | | | |
| $BaCl_2 . 2H_2O$ | 38.632 | g | | | |
| $CeO_2$ | 50.0 | g | | | |
| $Nd_2O_3$ | 25.0 | g | | | |
| $Y_2O_3$ | 6.566 | g | | | |
| $Sm_2O_3$ | 3.740 | g | | | |
| $Nb_2O_5$ | 75.0 | g | | | |

| Reaction Mixture: | | | | | |
|---|---|---|---|---|---|
| EXAMPLE | 1 | 2 | 3 | 4 | 5 |
| Distilled water ml. | 2750 | 2750 | 2500 | 2750 | 10,000 |
| Oxalic acid g. | 210 | 215 | 170 | 210 | 840 |
| Isopropyl alcohol ml. | 250 | 200 | 200 | 200 | 680 |
| 85% $H_3PO_4$ ml. | 227.7 | 231.0 | 227.7 | 229.1 | 1056.8 |
| HCl ml. | — | — | 100 | — | 400 |

PROCEDURE, EXAMPLES 1-4 (Note - Example 5 is conducted on scale approximately four times that of Examples 1-4, and the procedure should be adjusted accordingly.)

Heat the mixture to 50°–60° C. and add the $V_2O_5$ slowly while raising the temperature to 65° C. to 85° C. After all of the $V_2O_5$ is added, reflux slowly until the solution is homogeneous and blue. Reduce the volume to 1500 ml. by taking off water and alcohol on reflux. Add the $MoO_3$ to the vanadyl phosphate solution and continue to reflux and reduce the volume to about 1000 ml. The $Nb_2O_5$ is added to a tumbler, about 20 liter size, and prewarmed to 40°–60° C. The concentrated V-P-Mo mixture is then added to the tumbler. The heat source is increased to raise the temperatures to 75°–90° C. and held there. The NiO is dissolved in 400 ml. of HCl along with the $CoCl_2.6H_2O$. The oxides are digested to the soluble chlorides while reducing the HCl volume to 200 ml., 100 ml. of $H_2O$ is added to the clear, dark solution. The Ni-Co mixture is then added to the V-P-Mo-$Nb_2O_5$ mixture in the tumbler. The $CuCl_2.2H_2O$ is dissolved in 400 ml. of $H_2O$ and is added next; followed by $CrO_3$ in 50 ml. of $H_2O$. When the mixture becomes green and slightly viscous, $Nd_2O_3$, dissolved in $H_2O$ and HCl and $CeO_2$, dissolved in concentrated HCl, are added along with $BaCl_2$ (if any) in $H_2O$, and shortly after this, the $HfO_2$, $Y_2O_3$, $Sm_2O_3$, $Tb_4O_7$ and/or $Eu_2O_3$ (as appropriate) are added. After heating and loss of water vapor, the mixture becomes more viscous and difficult to stir. It is then transferred to pyrex dishes. The green mixture is dried from 85° C. to 100° to 135° C. over a 36-hour period. The solid mass is broken up to a 4 mesh, or less, and dried from 120° to 300° C. over 4 hours; held at 300° C. for one hour. The chipped catalyst is ball-milled in a dry atmosphere for 6 hours to obtain 60 mesh fines. To this is mixed 0.5% Curtin type graphite and 1% Baker stearic acid. ⅛"×⅛" pellets are produced. The pellets are heated slowly to 300° C. so that they can be added directly to the hot salt reactor held at 250° C.

The conditions of the reactors and results of maleic anhydride preparation from n-butane are set out below in Table I.

TABLE I

| Example | Catalyst | | Reactor Size | Temperature | | Butane | | Maleic Anhydride Mole % | | | Output g.MA/l.cat/hr | Ratio (g.MA Out / g.Butane In) |
|---|---|---|---|---|---|---|---|---|---|---|---|---|
| | ml. | dia. | | Salt | Hot Spot | Conc. Mole % | Thruput g/l cat/hr | Conv. | Sel | Yield | | |
| 1 | 300 | ⅛"×⅛" | ¾"×3' | 396 | 408 | 1.10 | 74 | 68 | 59 | 40 | 50 | 0.68 |
| | | | | 403 | 429 | 1.43 | 140 | 71 | 56 | 40 | 93 | 0.66 |
| 2 | 300 | ⅛"×⅛" | ¾"×3' | 398 | 409 | 1.05 | 66 | 71 | 62 | 44 | 49 | 0.74 |
| | | | | 407 | 449 | 1.29 | 150 | 70 | 62 | 43 | 109 | 0.72 |
| 3 | 300 | ⅛"×⅛" | ¾"×3' | 399 | 415 | 1.01 | 66 | 70 | 58 | 40 | 44 | 0.66 |

TABLE I-continued

| Example | Catalyst ml. | dia. | Reactor Size | Temperature Salt | Temperature Hot Spot | Butane Conc. Mole % | Butane Thruput g/l cat/hr | Maleic Anhydride Conv. | Maleic Anhydride Sel | Maleic Anhydride Yield | Output g.MA/ l.cat/hr | Ratio (g.MA Out / g.Butane In) |
|---|---|---|---|---|---|---|---|---|---|---|---|---|
| | | | | 402 | 440 | 1.33 | 132 | 71 | 55 | 39 | 87 | 0.66 |
| 4 | 300 | ⅛" × ⅛" | ¾" × 3' | 400 | 422 | 1.02 | 50 | 72 | 62 | 45 | 38 | 0.76 |
| | | | | 403 | 429 | 1.25 | 140 | 63 | 62 | 39 | 92 | 0.66 |
| 5 | 1850 | 3/16" × 3/16" | 1¼" × 12' | 389 | 421 | 1.40 | 87 | 69 | 67 | 46 | 68 | 0.78 |
| | | | | 388 | 422 | 1.45 | 91 | 69 | 67 | 46 | 71 | 0.78 |
| | | | | 392 | 430 | 1.63 | 96 | 73 | 66 | 48 | 79 | 0.82 |

These new catalysts are in every way at least equal to those disclosed in my commonly assigned U.S. Pat. No. 4,056,487, and are superior to many of those prior catalysts. Note, in particular, the present catalyst of Example 5, which exhibits excellent conversion for this reaction and superior selectivity for MA. Although the conditions of Example 5 were not extended to the same degree as the other examples, the ratio of MA output to butane input is highest for Example 5.

Butane was extensively employed in the present examples because of its availability and easy handling. The other $C_4$-$C_{10}$ hydrocarbons, particularly, normal paraffins and olefins, also are suitable for use in conjunction with the present catalyst to produce anhydrides; for example, n-pentane, n-hexane, n-heptane, n-octane, n-nonane and n-decane and the corresponding olefins.

The invention claimed is:

1. A process for the partial oxidation of $C_4$ to $C_{10}$ hydrocarbons comprising contacting a feed comprising $C_4$ to $C_{10}$ alkane hydrocarbons in vapor phase at elevated temperatures, with oxygen and a catalyst composition consisting of vanadium, phosphorus and oxygen and a modifying component of (a) Nb, Cu, Mo, Ni, Co and Cr, (b) one or more of the elements selected from the group consisting of Ce, Nd, Ba, Hf, U, Ru, Re, Li or Mg, and (c) one or more of the elements selected from the group consisting of Y, Sm, Tb, and Eu, wherein the atomic ratio of vanadium: phosphorus: Nb:Cu:Mo:Ni:-Co:Ce:Nd:Cr:Ba:Hf:U:Ru:Re:Li:Mg:Y:Sm:Tb:Eu is 1:0.90 to 1.3: 0.001 to 0.125:0.022 to 0.201:0.0025 to 0.040:0.0022 to 0.045:0.004 to 0.066:0.0054 to 0.20:0.0022 to 0.20:0.0003 to 0.003:0.0023 to 0.0585:0.0023 to 0.0409:0.0033 to 0.0993:0.0002 to 0.02015:0.0002 to 0.0074:0.0072 to 0.179:0.0088 to 0.222:0.0001 to 0.02:0.0001 to 0.02:0.0001 to 0.02, respectively, the total atomic ratio of Nb, Cu, Mo, Ni, Co, Ce, Nd, Cr, Ba, Hf, U, Ru, Re, Li, Mg, Y, Sm, Tb and Eu being in the range of 0.033 to 0.4.

2. The process according to claim 1 wherein said hydrocarbons is a normal hydrocarbon.

3. The process according to claim 2 wherein said normal alkane is n-butane.

4. The process according to claim 1 wherein the modifying component is Nb, Cu, Mo, Ni, Co, Ce, Nd, Cr, Ba, Hf and Y.

5. The process according to claim 1 wherein the modifying component is Nb, Cu, Mo, Ni, Co, Ce, Nd, Cr, Ba, Y and Sm.

6. The process according to claim 1 wherein the modifying component is (a) Nb, Cu, Mo, Ni, Co, and Cr, (b) one or more of Ce, Nd or Ba and (c) one or more of Y, Sm, Tb or Eu.

7. The process according to claim 1 wherein said hydrocarbon comprising about 88 to 99 mol percent normal $C_4$ alkanes and from about 1 to 12 mol percent n-butene, benzene or a mixture thereof.

8. The process according to claim 4 wherein the atomic ratio of vanadium:phosphorus:Nb:Cu:Mo:Ni:-Co:Ce:Nd:Cr:Ba:Hf:Y is 1:0.90 to 1.3:0.001 to 0.125:0.022 to 0.201:0.0025 to 0.4:0.0022 to 0.045:0.0040 to 0.066:0.0054 to 0.20:0.0022 to 0.2:0.0003 to 0.003:0.0023 to 0.0585:0.0023 to 0.0409:0.0001 to 0.02, respectively.

9. The process according to claim 5 wherein the atomic ratio of vanadium:phosphorus:Nb:Cu:Mo;Ni:-Co:Ce:Nd:Cr:Ba:Y:Sm is 1:0.90 to 1.3:0.001 to 0.125:0.022 to 0.201:0.0025 to 0.04:0.0022 to 0.045:0.0040 to 0.066:0.0054 to 0.20:0.0022 to 0.20:0.0003 to 0.003:0.0023 to 0.0585:0.0001 to 0.02, respectively.

10. The process according to claim 6 wherein the atomic ratio of vanadium:phosphorus:Nb:Cu:Mo:Ni:-Co:Cr:Ce:Nd:Ba:Y:Sm:Tb:Eu is 1:0.90 to 1.3:0.001 to 0.125:0.022 to 0.201:0.0025 to 0.040:0.0022 to 0.045:0.0040 to 0.066:0.0003 to 0.003:0.0054 to 0.20:0.0022 to 0.2:0.0023 to 0.0585:0.0001 to 0.02:0.0001 to 0.02:0.0001 to 0.02:0.0001 to 0.02 respectively.

* * * * *

UNITED STATES PATENT AND TRADEMARK OFFICE
CERTIFICATE OF CORRECTION

PATENT NO. : 4,202,826
DATED : May 13, 1980
INVENTOR(S) : Ralph O. Kerr

It is certified that error appears in the above—identified patent and that said Letters Patent is hereby corrected as shown below:

Col. 2, line 22 reads "B" but should read -- Ba --

Col. 2, line 35 reads "1.3, b is" but should read -- 1.3 and b is --

Col. 4, line 15 reads "been given" but should read -- given --

Col. 4, line 29 reads "and metallid" but should read -- and metalloid --

Col. 7, line 49 reads "proer temperature" but should read -- proper temperature --

Col. 10, line 16 reads "on scale" but should read -- on a scale --

Signed and Sealed this

Tenth Day of February 1981

[SEAL]

Attest:

Attesting Officer

RENE D. TEGTMEYER
Acting Commissioner of Patents and Trademarks